United States Patent
Dubois et al.

(10) Patent No.: US 8,877,948 B2
(45) Date of Patent: Nov. 4, 2014

(54) SYNTHESIS PROCESS OF POLYOL CARBONATE FROM POLYOLS, CONDUCTED IN USING A SOLVENT SELECTIVE FOR POLYOLS CARBONATES

(75) Inventors: Jean-Luc Dubois, Millery (FR); Michele Aresta, Bari (IT); Angela Dibenedetto, Altamura (IT); Carla Ferragina, Rome (IT); Francesco Nocito, Taranto (IT)

(73) Assignee: Arkema France, Colombes (FR)

( * ) Notice: Subject to any disclaimer, the term of this patent is extended or adjusted under 35 U.S.C. 154(b) by 861 days.

(21) Appl. No.: 13/122,597

(22) PCT Filed: Oct. 7, 2009

(86) PCT No.: PCT/EP2009/063056
§ 371 (c)(1),
(2), (4) Date: Jun. 20, 2011

(87) PCT Pub. No.: WO2010/040786
PCT Pub. Date: Apr. 15, 2010

(65) Prior Publication Data
US 2011/0245513 A1    Oct. 6, 2011

(30) Foreign Application Priority Data
Oct. 8, 2008  (EP) ................... 08305653

(51) Int. Cl.
*C07D 317/08* (2006.01)
*C07D 317/36* (2006.01)

(52) U.S. Cl.
CPC .................... *C07D 317/36* (2013.01)
USPC .......................................... 549/229

(58) Field of Classification Search
CPC C07D 317/36; B01J 2523/48; B01J 2523/47; B01J 21/063; B01J 21/066
USPC ........................................ 549/229
See application file for complete search history.

(56) References Cited

U.S. PATENT DOCUMENTS

| | | |
|---|---|---|
| 5,003,084 A | 3/1991 | Su et al. |
| 5,349,007 A | 9/1994 | Serizawa et al. |
| 5,359,094 A | 10/1994 | Teles et al. |
| 6,025,504 A | 2/2000 | Claude et al. |
| 6,495,703 B1 | 12/2002 | Okutsu et al. |

OTHER PUBLICATIONS

Yoo, J.-W., et al., Catalytic Carbonylation of Glycerin by Urea in Pressence of Zinc Mesoporous System for the Synthesis of Glycerol Carbonate, Studies in Surface Science and Catalysis, vol. 146, pp. 757-760, 2003.

*Primary Examiner* — T. Victor Oh
(74) *Attorney, Agent, or Firm* — Smith, Gambrell & Russell, LLP

(57) ABSTRACT

The present invention relates to a synthesis process of polyol carbonate, such as glycerol carbonate, from polyols such as glycerol, propylene glycol or ethylene glycol and urea conducted in using a solvent selective for polyols (glycerol) carbonates. Said process comprises reacting polyol with urea in the presence of a catalyst, extracting produced $NH_3$ and in addition in the presence in the course of at least one step of the process of a selective solvent for polyol carbonate allowing to extract it from the reaction medium.

19 Claims, No Drawings

SYNTHESIS PROCESS OF POLYOL CARBONATE FROM POLYOLS, CONDUCTED IN USING A SOLVENT SELECTIVE FOR POLYOLS CARBONATES

FIELD OF THE INVENTION

The present invention relates to a synthesis process of polyol carbonate, such as glycerol carbonate, from polyols such as glycerol, propylene glycol or ethylene glycol and urea conducted in using a solvent selective for polyols (glycerol) carbonates.

BACKGROUND OF THE INVENTION

The synthesis of glycerol carbonate was described for years. A reaction of glycerol with phosgene and an exchange reaction of glycerol with a dialkyl carbonate are known as conventional methods for synthesizing glycerol carbonate from glycerol. Another method for synthesizing glycerol carbonate consisting in reacting glycerol with carbon monoxide and oxygen at a high pressure is described in U.S. Pat. No. 5,359,094. More recently a new way has been proposed based on the reaction of glycerol with urea according to the global reaction as follows:

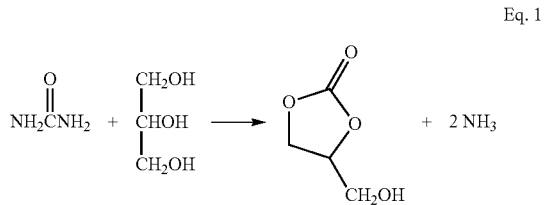

Eq. 1

In practice this reaction is the result of two steps according to the following mechanism:

1) CH$_2$OH—CHOH—CH$_2$OH + NH$_2$—CO—NH$_2$ <=> CH$_2$OH—CHOH—CH$_2$O—CO—NH$_2$ + NH$_3$

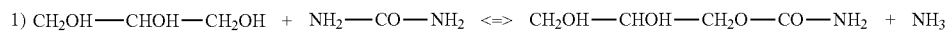

2) CH$_2$OH—CHOH—CH$_2$O—CO—NH$_2$ <=> 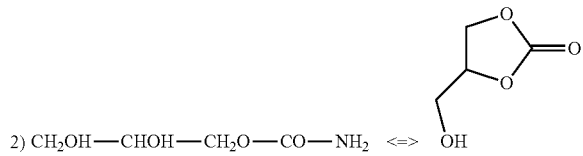 + NH$_3$

Both reactions are reversible. It means that in order to reach the total conversion of reagents into glycerol carbonate, the equilibrium of the reaction has to be shifted towards the right. The classical solution is the extraction of NH$_3$ from the reaction medium under vacuum.

This kind of process is described in recent patents: EP 0 955 298 (ONIDOL) and 1 156 042 (KAO) and in addition in the article of J-W. Yoo and Z. Mouloungui <<Catalytic carbonylation of glycerin by urea in presence of zinc mesoporous system for the synthesis of glycerol carbonate>> in *Studies in Surface Science and Catalysis* 146 pages 757-760 Park et al (Editors) 2003.

These documents describe the operating conditions of the process.

According to EP 0 955 298, the process is conducted at a temperature comprised between 90° C. and 220° C. and at a pressure comprised between 1 and 20 kPa, in presence of a catalyst comprising Lewis acids sites with their anionic counterpart provided by heteroatoms. Examples of said catalysts are metallic or organometallic sulfates, such as MnSO$_4$, ZnSO$_4$, MgSO$_4$, FeSO$_4$ or hydrate of paratoluene zinc sulfate for example which are possibly associated with a support.

According to EP 1 156 042 the reaction is generally conducted in the presence of a catalyst such as a metal oxide (zinc oxide) and preferably carried out in the presence of a dehydrating agent such as anhydrous magnesium sulfate, anhydrous sodium sulfate, anhydrous calcium sulfate or a molecular sieve, in order to ensure the quality of glycerol, at a temperature comprised between 100° C. and 140° C. and at a reduced pressure comprised between 13.3 and 101 kPa.

The here-above cited article concerns the works carried out by the research team having previously leaded to the filing of EP 0 955 298. The article is dedicated to various catalyst systems using Zn as active element. These systems are heterogeneous or homogeneous. For heterogeneous systems Zinc (ZnSO$_4$) is in the form of a mineral salt or associated with an acidic resin or on an aluminosilicate. In the homogeneous form, Zn is present as a p-toluene-sulphonate. The molar yields in glycerol carbonate reach about 80%. The experiments are conducted at a temperature of 130-150° C. under a pressure of 4 kPa. The processes described in these patents present some drawbacks. The used reagents, glycerol and urea, lead to a viscous mixture which has to be vigorously stirred in order to obtain a correct contact between the reagents and the catalyst and to provide an efficient mass transfer for ammonia removal. Moreover, such slurry does not allow an easy recovery of glycerol carbonate and recycling of the catalyst. This contact will be better when the catalyst is under homogeneous form. However in that case the separation of the catalyst from the produced glycerol carbonate contained within the reaction medium is rather problematic. Such a process carried out in batch mode cannot be implemented economically on an industrial scale considering in addition the reduced pressure conditions required to remove ammonia.

DETAILED DESCRIPTION OF THE INVENTION

The invention is directed to a process allowing to overcome the drawbacks of the previous processes in using a solvent in the course of at least one step of the whole process allowing particularly to easily separate the glycerol carbonate from the reaction media. The invention will apply as well to the polyol carbonates prepared by reaction of the urea with ethanediol also called ethylene glycol, propandiol-1,2 also called propylene glycol or propandiol-1,3 (polyols). In order to simplify the following description the terms glycerol and glycerol carbonate will design respectively glycerol or polyol and glycerol carbonate or polyol carbonate as well. The physical characteristics of these compounds are given in the following Table 1.

TABLE 1

| Polyol | Boiling point (° C.) | CAS RN | Density $d_4^{20}$ (g/cm³) |
|---|---|---|---|
| 1,2-Ethane diol, Ethylene glycol | 197.3 | 107-21-1 | 1.1088 |
| 1,2-Propane diol, Propylen glycol | 187.6 | 57-55-6 | 1.0361 |
| 1,3-Propane diol | 214.4 | 504-63-2 | 1.0538 |
| Glycerol | 290 | 56-81-5 | 1.2613 |
| Ethylene Carbonate | 246 | 96-49-1 | 1.321 |
| Propylene Carbonate | 241 | 108-32-7 | 1.204 |
| Glycerol Carbonate | 110-115° C. at 0.1 mmHg | 931-40-8 | 1.4 |

The invention relates to a process for synthesizing polyol carbonate which comprises reacting polyol with urea in the presence of a heterogeneous or homogeneous catalyst with a continuous extraction of the produced $NH_3$ and in addition, combining in the course of the process at least one step, of a selective solvent for polyol carbonate allowing to extract it from the reaction medium.

As a consequence, the present invention deals with a process for synthesizing polyol carbonate which comprises reacting polyol with urea in the presence of a catalyst, extracting produced $NH_3$ and in addition in the presence in the course of at least one step of the process of a selective solvent for polyol carbonate allowing to extract it from the reaction medium.

Selective solvent for polyol carbonate means that this solvent is able to form a stable solution with polyol carbonate i.e. solvent in which polyol carbonate is soluble in all ratios without dissolving polyol and urea or at least having a very low dissolving capacity of such compounds.

More specifically selective presents a solubility for polyol carbonate as compared with its solubilities for polyol and urea such as the ratios polyol solubility/polyol carbonate solubility and urea solubility/polyol carbonate solubility are respectively less than 8% and 15% and preferably less than 2% and 10%.

The selective solvents used in the process of the invention are chosen amongst the compounds comprising at least a function nitrile or ketone and meeting the here-above conditions.

Examples of selective solvents according to the invention are given in Table 2 including their main physical characteristics, solubilities being given at 25° C.

TABLE 2

| Solvent | $d^{20}_4$ | Solubility of Glycerol Carbonate g/mL | Solubility of Glycerol g/mL | Solubility of Urea g/mL | Boiling point at 0.1 MPa ° C. |
|---|---|---|---|---|---|
| Acetophenone | 1.03 $d^{15}_{15}$ | >0.5 | 0.011 | <0.004 | 202 |
| Acetonitrile | 0.78 | >0.5 | 0.002 | <0.001 | 82 |
| Cyclohexanone | | >0.5 | 0.026 | <0.004 | 155 |
| Diethylketone | 0.81 | >0.5 | 0.040 | <0.004 | 103 |
| Isophorone | | | | | 213 |
| Metacrylonitrile | | >0.5 | 0.010 | <0.004 | 92 |
| Methylethylketone | 0.80 | >0.5 | 0.043 | <0.004 | 79.6 |
| N-methyl-pyrrolidone | | >0.5 | 0.15 | 0.05 | 202 |
| Propionitrile | 0.78 | >0.5 | 0.016 | <0.004 | 97 |
| Butyronitrile | 0.79 | | | | 118 |
| Isobutyronitrile | 0.77 | >0.5 | 0.01 | 0.06 | 107 |
| Pentanenitrile (Valeronitrile) | 0.80 | | | | 139-141 |
| Isovaleronitrile | 0.79 | >0.5 | 0.008 | 0.058 | 130 |
| Hexanenitrile | 0.81 | | | | 162 |
| Pentanenitrile, 4 Methyl | 0.8 | | | | 154 |
| Heptanenitrile | 0.81 | | | | 186-187 |
| Dimethylmalonitrile | | | | | 169.5 |
| Crotonitrile | | | | | 120-121 |
| Fumaronitrile | | | | | 186 |

Of course the selectivity is an essential characteristic in choosing the selective solvent (also named extracting solvent) to be used. However it is not the only one.

A selecting criteria for the selective solvent is its boiling point. This later has to be i) high enough if to be used within the reaction medium at the operating reaction temperature, between 130 and 145° C. for instance, without solvent losses but, ii) not too high i.e. not near the boiling point of produced polyol carbonate in order to avoid separation problems. Low boiling selective solvents i.e. <130° C. are very efficient as extracting agent but lead to some problems of losses when used within the reactor at "severe" operating conditions conducting to the use of costly trapping conditions.

For instance Acetophenone has a good selectivity and a high boiling point that allows to carry out the reaction at 145° C. with a good conversion of polyol without solvent losses.

The selected solvent has also to be non-reactive either with the reagents or the used catalysts. Considering Acetophenone, this latter slightly reacts at 145° C. with urea. That means that when it is used in the reaction medium for a long period it leads to several by-products that remain in the solvent which may contaminate the polyol carbonate. When ketones are used as selective solvents within a process using an acidic catalyst and glycerol they possibly lead to glycerol acetals, while releasing water which in turn can interfere with the glycerol carbonate synthesis.

Another selecting criteria for the selective solvent is its density which has to be very different from the glycerol density (1.2613), main reactive solvent of the reaction, in order to make easier the phases separation. The ratio solvent density/polyol density will be preferably less than 0.85 and more preferably less than 0.8. In case of Glycerol as polyol, the ratio will be even more preferably less than 0.7. The final selection of the convenient selective solvent also depends on the mode for conducting the process and the operating temperature.

The preferred selective solvents to be used are the solvent comprising a nitrile function.

The most preferred selective solvents are acetonitrile, propionitrile and iso-valeronitrile, as they are quite selective for the carbonate, do not give any extended interaction with the other components of the reacting mixture and are easily separated from the carbonate solution by distillation. Heptanenitrile, for example, is a well suited high boiling point solvent which can be used within the reaction, when the reaction is carried out below its boiling point, for example at 140° C., since its continuous evaporation will be limited, and it can be easily recycled to the reactor. Separation from polyol carbonate, can be done by vacuum distillation.

The reaction is preferably conducted at a temperature comprised between 90° C. and 200° C., preferably at a temperature of 100 to 150° C. and more preferably at about 130-145° C.

The reaction is generally carried out under a pressure comprised between 2 and 200 kPa, preferably under a pressure comprised between 4 and 150 kPa and more preferably between 10 and 120 kPa. The pressure conditions essentially depends on the mode selected for conducting the reaction.

The process will be conducted with any catalyst known to be efficient within the synthesis of polyol carbonate by reacting polyol with urea and especially with heterogeneous catalysts which are in practice easier to handle on an industrial scale than the homogeneous ones. By heterogeneous catalyst one should understand a catalyst solid at the operating conditions, such as the catalysts described in the here-above referenced patents: ZnO, $MnSO_4$, $ZnSO_4$, $MgSO_4$, $FeSO_4$.— and the here below described Zr or Ti catalysts which are another feature of the present invention. The heterogeneous catalysts can be easily separated form the medium or reused in the same medium for another step of conversion of polyol with urea. The homogeneous catalysts must be insoluble into the extraction solvent i.e. a solubility<5 wt %, otherwise they will be lost after each extraction.

Another feature of the invention is directed to heterogeneous catalysts particularly effective in the process of the invention. In this process several catalysts were used of the family of compounds with a pillared layered structure, such as α and γ-Zr-phosphate or amorphous and γ-Ti-phosphate. The results reported below in the examples are relevant to α-Zr-phosphate (Catalyst 1) and γ-Zr-phosphate (catalyst 2), its dehydrated form (Catalyst 2a) obtained by treatment of the former for two hours at 140° C. Also, the γ-Ti-phosphate and the relevant dehydrated forms were used and presented a similar activity. The catalysts were prepared according to the method reported below. (For structural information about the catalysts see also: S. Allulli, C. Ferragina, A. La Ginestra, M. A. Massucci and N. Tomassini, "Preparation and ion-exchange properties of a new phase of the crystalline titanium phosphate $Ti(HPO_4)_2,2H_2O$" *J. Inorg. Nucl. Chem.*, vol. 39, pg. 1043-1048, 1977; and references therein).

The catalysts so described are resistant to the reaction conditions and do not dissolve neither destroy under stirring. They remain in the polyol phase as a solid well separated from the liquid phase: it can be time to time separated, washed and re-activated, if necessary.

Accordingly, the present invention also relates to a process for synthesizing polyol carbonate which comprises reacting polyol with urea in the presence of a catalyst constituted by γ-Zr-phosphate or γ-Ti-phosphate and extracting produced $NH_3$.

The process can be conducted either according to a "compact" mode in which the catalytic reaction polyol-urea is carried out in the presence of the selective solvent or a "sequential" mode in which the reaction is only carried out with the reagents and the resulting reaction medium is treated in an independent zone (extracting zone) by the selective solvent for extracting the carbonate.

Both modes can be conducted either according to a continuous or discontinuous way.

According to the invention the continuous compact mode consists in a kind of extractive reaction in the course of which the reagents, glycerol and urea and selective solvent are continuously introduced into the reactor containing the catalyst and working under agitation at the chosen operating conditions. The reaction glycerol+urea conducting to glycerol carbonate and dissolving this latter within the selective solvent are concomitant. Reaction and extraction of the carbonate solution are simultaneous.

The process can be carried out within a reactor having a top part constituted as a distillation column and in which the reagents (polyol and urea) are introduced into the column at in intermediate level in direct contact with the catalyst located within the column and the selective solvent introduced at the upper part of the reactor. The solution of carbonate is extracted from lower part of the reactor. The non converted glycerol is recovered and recycled with the fresh reactants. The carbonate solution is distilled in order to recover the carbonate and to recycle the selective solvent.

In an other configuration of reactor, the mixture of polyol and urea is reacted on a catalyst in the presence of the extraction solvent in an agitated reactor subdivided in 2 section separated by a wall. Reactants are fed by the bottom of the reactor and flow through the reactive zone. The solvent fraction containing polyol carbonate moves to the upper layer and overflow in the second part of the reactor where the mixture is no longer agitated. In this part, the bottom layer rich in polyol is recycled to the reaction zone, and the upper layer containing solvent and polyol carbonate is withdrawn and sent to the distillation unit where the solvent is recovered and recycled to the reactor.

The same compact process mode can be conducted according to a discontinuous way. In such a case the reaction polyol-urea in presence of the catalyst and the selective solvent is pursued for a period of time (a run) defined so that an optimum reaction rate/selectivity is reached. At the term of this run the stirring is stopped. The mixture settles and the upper phase (solution of carbonate within selective solvent) is extracted by any convenient way, suction for instance to be submitted to a distillation to recover the carbonate. The remaining bottom phase containing both non converted reagents and catalyst is ready for a new run after addition of fresh reagents and selective solvent. Selective solvent recovered after distillation may constitute a part of added selective solvent for a new run. The same operations may be repeated several times.

According to the invention the discontinuous sequential mode consists in carrying out the reaction polyol-urea in presence of the catalyst in an agitated reactor for a run as here above defined.

At the term of the run the whole reaction medium is transferred into a separation vessel (extracting zone) cooled and stirred after addition a suited volume of selective solvent. After stopping stirring the mixture splits off into two phases, the upper phase consisting in the carbonate solution. The upper phase is separated from the bottom one either by settling of the bottom one or by suction of the upper one. The final steps here above described for compact mode will allow to recover on one hand the carbonate and selective solvent and on other hand the residual reaction medium (non converted reagents and catalyst) which can be used within a new run in the reactor.

Accordingly, in the discontinuous compact mode, the extraction of the carbonate solution is carried out at the term of each run.

The continuous sequential mode consists in carrying out the reaction polyol-urea in presence of the catalyst in an agitated reactor. After a period of time lower than the run as referred in the paragraph relating to the discontinuous sequential mode, a fraction of the reaction medium is taken and transferred into the separation vessel (extracting zone) in which it is submitted to the preceding extraction procedure while the reactor is completed with fresh additional reagents in order to maintain the initial content in said reagents. Of course reagents and selective solvent recovered from the extraction procedure can be used respectively as fresh reagent and extracting solvent.

Accordingly, in particular embodiments, the process is conducted in a sequenced mode in which the catalytic reaction is carried out without the selective solvent and the reaction medium is transferred into an independent zone where the selective solvent is added. Said process can be conducted in a discontinuous sequenced mode in which the whole reaction medium is transferred into the independent zone where the selective solvent is added. Additionally, said process can be conducted in a continuous sequenced mode in which only a part of reaction medium is transferred into the independent zone where the selective solvent is added, fresh reagents being introduced into the reactor in order to maintain its level of reagents.

Of course the selective solvents used into the two different modes are different in considering their boiling points.

Within the contact mode process, continuous or discontinuous, the selective solvent must have a boiling point high enough to keep it in contact within the reaction medium at the operating conditions. In such a case iso-valeronitrile (130° C.), valeronitrile (139-141° C.), hexanenitrile (162° C.), heptanenitrile (186° C.)) and acetophenone (202° C.) are convenient for conducting the process. The selection amongst these solvent will depend on the other criteria: density in order to make easier the decanting separation, possible reactivity with reagents (by-products).

Within the sequenced mode process, continuous or discontinuous, the boiling point selection criteria for the selective solvent is not essential. However in order to make easier the distillation applied on the carbonate solution (last step of the process) it is advantageous to use a selective solvent having a low boiling point such as acetonitrile and propionitrile which positively correspond to the other criteria. The extraction of the carbonate is carried out quantitatively, without a real contamination by polyol or urea.

The reaction is generally carried out under a pressure comprised between 2 and 200 kPa. The two modes, compact and sequenced, of reaction can be carried out within this pressure range.

However in practice the sequenced one is generally conducted within a pressure range comprised between 2 and 100 kPa and preferably between 4 and 20 kPa in order to allow ammonia to easily escape from the reaction liquid phase. Concerning the compact mode the preferred pressure range is comprised between 30 and 200 kPa and more preferably between 60 and 150 kPa.

For instance in case of use of iso-valeronitrile within a compact continuous mode conducting the reaction at 130° C. (boiling point of isovaleronitrile) under atmospheric pressure (100 kPa) interesting results can be reached the vapors of the solvent allowing to drive off the ammonia produced in addition to its own action as extracting solvent for carbonate. If a condenser is used on top of the reactor, the solvent can be recycled to the reactor continuously and ammonia escapes the reaction medium and can be trapped in water (or in a cooled bath). Of course a $N_2$ flux can be used for a better elimination of $NH_3$.

A significant advantage of the invention is to be able to conduct the process at a pressure near the atmospheric pressure and even at a pressure slightly higher.

The reaction is conducted with an initial excess of polyol in comparison with the stoichiometry of the reaction, the polyol in excess being the reactive solvent medium of the reaction. The starting molar ratios polyol-urea are comprised between 1/1 and 6/1 and preferably between 1/1 and 2/1.

The conversion of polyol strongly depends on such molar ratio. The minimum starting ratio polyol/urea for a good conversion of the polyol resulted to be 2/1 when a discontinuous mode was used. It is possible to use a technique that allows to minimize the polyol/urea ratio. Starting with a polyol/urea=2/1, after a first catalytic run and then the addition of a selective solvent, the solution of polyol carbonate was extracted and either only urea or equimolar amounts of urea and polyol were added to the remaining solution constituting the reaction medium containing the catalyst for a second run. In the latter case the overall polyol/urea ratio became 3/2 (=(2+1)/(1+1)); the procedure was repeated and for the third run the overall polyol/urea ratio was 1.33/1=(2+1+1)/(1+1+1) and so on for several runs with a decreasing polyol/urea ratio. The real overall benefit provided by this technique is practically restricted to three/four runs because the residual polyol carbonate left in the reaction medium after the extractions has a tendency to react with urea causing the accumulation of by-products. Of course after separation of the polyol carbonate by distillation the recovered selective solvent is reused within the next runs.

Each run is conducted for a time ranging from one to three hours. A short time of reaction leads to a low yield while a long reaction time decreases the selectivity towards the polyol carbonate as the latter undergoes a reaction with urea leading to undesired by products. Therefore, the best conditions that maximize the yield and minimize the by-product formation are found for a reaction time generally comprised between two and three hours.

Working in a compact discontinuous process mode, better results will be obtained as the recycle system may reduce the accumulation of said by-products. In this case, the selective solvent used will have a high boiling point allowing to conduct the reaction at high temperature but might create by-products by reacting with one of the reaction components. Anyway, by choosing the most appropriate solvent, impurities are practically limited to a few units percent (3-5%) with respect to polyol if the number of cycles is kept around 3-4 and excess polyol carbonate in the reaction solution is avoided.

The efficiency of the compact continuous extraction mode that operates for instance at 100 kPa strongly depends on the diffusion of ammonia out of the reaction medium and reactor. Depending on the design of the reactor, the use of a very slow flow stream of $N_2$ can be beneficial for the extraction/stripping of ammonia that otherwise may stagnate within the reactor and retro-diffuse to the reacting medium. Alternatively, the ammonia can be pumped before being directed to a water trap or compressed and cooled down to be stored as liquid ammonia.

In any compact mode conducted at the ambient atmospheric pressure, the reaction flask is connected to a condenser cooled at 20 to −20° C. that allows to condense the extracting solvent and avoid that it is lost with $NH_3$. The cold finger temperature depends on the boiling point of the selective solvent: using isovaleronitrile or acetophenone it can be cooled at 20° C. using water. When low boiling selective solvents are used it is better to keep the temperature of the cold finger at −20° C. in order to avoid large solvent loss. The final separation of the two phases is simply carried out by decantation of the extracting solvent or by using a reparatory funnel.

The invention relates also to a process for synthesizing polyol carbonate which comprises reacting polyol with urea in a solvent medium made of polyol in the presence of a preferably fully recoverable heterogeneous catalyst, and a selective solvent for polyol carbonate that selectively extracts the polyol carbonate with elimination of ammonia either in vacuum or by using the vapors of the extracting solvent and, possibly, a slow flow of $N_2$ as carrier for its extraction from the reactor. This methodology is not really suited for low boiling solvents such as acetonitrile or propionitrile; it is better suited for solvents having a boiling point of about or higher than 130° C.

This version of the process in which the formed polyol carbonate passing into the selective solvent phase and consequently leaving the reaction medium, allows to shift the reaction equilibrium towards the right and consequently to increase the conversion of polyol without using reduced (low) pressure conditions. In addition to shift continuously the equilibrium towards the right by ammonia abstraction from the reaction medium, polyol carbonate is continuously extracted from the reaction medium. This effect can be obtained either when the reaction is done in the presence of the selective solvent, or when the reaction and the extraction are carried out according to the sequenced mode, with recycling of the non converted reagents and catalyst back to the reactor for a new run.

Selective solvent will be chosen among those in Table 2. Preferably when the selective solvent is used in the reaction medium, the solvent will be selected among nitriles. The reaction time must be chosen in such a way of reducing the contact of urea with polyol carbonate as they can react with an attack of urea on the carbonylic carbon. Therefore, the extension of the reaction time when polyol carbonate and urea are co-present in the reaction mixture increases the formation of by-products. The selectivity (towards the carbonate) and the extraction efficiency play, thus, a key role in determining the overall polyol conversion yield into the carbonate.

Several reactor/separator technologies can be used to achieve the objectives of the present invention.

Examples of reactor technologies include the thin film evaporator, short path distillation unit (ex Tournaire http://www.tournaire-equipment.com, UIC GmbH /www.uic-gmbh.de and Gigkarasek www.gigkarasek.at) and spinning disk reactor (Protensive, www.protensive.co.uk) for which there is a high mass transfer rate, without requiring high temperatures. These technologies are appropriate either for the reactor with heterogeneous or "homogeneous" (slurry) catalysts or for the separation of the solvent and polyol carbonate.

There is also a Technology of centrifugal molecular distillation (see Myers-Vaccuum, Inc. www.myers-vaccuum.com).

A technology of rotating packed bed reactor (see Protensive, www.protensive.co.uk) can also be used with the heterogeneous catalyst. This reactor technology allows a high mass transfer rate.

The reactor technology of a long tubular reactor, with or without baffles, such as the Oscillatory Baffled Reactor (see for example NiTech Solutions www.nitechsolutions.co.uk) allows a near plug flow of reactants. The ammonia produced can be withdrawn from the reactor at intermediate stages.

Similarly a technology of Loop reactor (similar to the Buss Loop reactor) could be used, and in which the gas produced is continuously removed (vented). The high flow rate allows to keep a good dispersion of the reactants.

Finally, a technology of catalytic distillation can be considered in the case of the compact continuous mode where the reaction is done is the presence of the solvent. Polyol and Urea would be introduced at an intermediate level, the selective solvent being introduced in the upper levels. The top section would be used to cool the gas stream composed of ammonia and solvent, and working at total reflux of solvent.

The ammonia is recovered either as liquid ammonia through a cold loop, or as aqueous ammonia when being trapped in water. This is possible since a high ammonia partial pressure can be generated. In the reactive distillation, polyol and urea are going downward and meet with the catalyst (either homogeneous or heterogeneous) and react together producing polyol carbonate and ammonia. Polyol carbonate moves in the solvent phase and continues to move downward. At the bottom of the column, polyol carbonate accumulates in the solvent and is extracted and later separated from the solvent, which is recycled in the column.

In the reactor used according a compact mode there is mix of polyol-urea-solvent and catalyst. The solvent is selected so that its boiling point is near the reaction temperature (in the reaction conditions). As the temperature raises the solvent start to boil and created the gas stream that help to drive the ammonia off. In the condenser the solvent is recovered and in the cold trap ammonia is recovered (either as liquid $NH_3$ or as aqueous ammonia). Continuously the solvent mixture is removed from the reactor and decanted. Polyol-urea is returned to the reactor and the solution solvent-polyol carbonate is separated, and the solvent is recycled to the reactor.

The boiling point of ammonia depends on the pressure according to the following scale: 5.2 kPa: −79° C.; 11.9 kPa: −69° C.; 75.2 kPa: −39° C.; 125.9 kPa: −29° C.

It is then interesting to operate at the highest pressure and consequently with an ammonia partial pressure of more than 100 kPa to avoid to consume too much energy in cooling condensers Where it is possible to operate the reactor under pressure, the reactor temperature could be lower and allowing to use a larger range of selective solvents leading to an easier separation of polyol.

EXAMPLES

Preparation of the Catalysts

1) α-Zr-Phosphate, Catalyst 1

63.50 g of $ZrOCl_2.8H_2O$ were dissolved in 750 mL of water and to such solution 70 mL of HF 50% were added together with 675 mL of a solution containing 150 mL of $H_2O$ and 525 mL of $H_3PO_4$ 85%. The solution was boiled under reflux for 5/6 days until the precipitation was completed. The solid was filtered and washed with distilled water until complete removal of Cl⁻ ions (negative chloride test on washing waters). The precipitate was stored in a dryer over $P_2O_5$ at room temperature until constant weight (three days).

2) γ-ZrPhosphate, Catalyst 2 and Catalyst 2a 100 mL of $ZrOCl_2.8H_2O$ 1M were added dropwise to 200 mL of boiling solution of $NaH_2PO_4.H_2O$ 6M. The gel was divided in several portions each sealed with its mother liquor in a Pyrex glass tube and heated in an autoclave at 180° C. for a week. The formed crystals were separated and washed with HCl 1N to remove the Na⁺ ions and then with the minimum amount of distilled water until it resulted free from Cl⁻ ions (see example 1). The crystals were dried at 25° C. in the air over $P_2O_5$. This catalyst is reported as Catalyst 2. The catalyst labelled as Catalyst 2a—was Catalyst 2 heated for 2 hr at 140° C.

3) Amorphous Ti-Phosphate, Catalyst 3

1376 mL of $H_3PO_4$ 1.25M were added dropwise to a solution of 86 g of $TiCl_4$ mixed with 1479.25 mL of HCl 2N. After 24 h the precipitate formed was filtered and washed with distilled water added with HCl up to pH=3-3.5, and dried over $P_2O_5$.

4) γ-Ti-Phosphate, Catalyst 4

2.5 g of amorphous TiP prepared as in Example 3 were mixed with 35 mL of $H_3PO_4$ 10M. The solution was sealed in a Pyrex glass tube and heated in an autoclave at 300° C. for 48 h. The tubes were opened, the solid formed was filtered and washed with distilled water added with HCl (pH=5) and then with little distilled water to eliminate the chloride ions.

Catalysts 1 to 4 were used as such or else they were loaded with intercalated monovalent- or bivalent- and trivalent-cations of the Groups 2-14 [as an example we mention Zn(II), Pd(II), Pt(II), Ru(II), Sc(III), Rh(I) and Rh(III), others]. Preparation of Layered Phosphates Intercalated with Mono-Bi-Trivalent Cations.

The general procedure for loading a cation into the layered-pillared catalysts Catalysts 1, 2, 4 is reported below.

Catalyst 1, 2, or 4 was suspended in a solvent such as methanol and a solution of the cation (provided in the form of nitrate or chloride) was slowly added at a temperature of 25-45° C. The concentration of the cation in the solution was determined as a function of the expected loading charge. In general, at least the double of the amount of cation with respect to the loading charge was contacted with the solid matrix. The contact time ranged from 1 to 7 days at 25° C., according to the desired metal loading.

The solid was then filtered, washed with $CH_3OH$ and gently dried. The amount of intercalated metal was typically in the range 2-7%, and was determined by classic methods for elemental analysis.

Such catalysts, anyway did not perform better than the original materials Catalyst 1-4.

The here below examples describe the use of nitriles (acetonitrile, iso-valeronitrile) and ketone (acetophenone) as selective solvent. Glycerol carbonate is soluble in said solvents, while glycerol has a limited solubility from 2 to 11 mg $ml^{-1}$ and urea a limited solubility from 1 to 58 mg $ml^{-1}$.

Example 1

In a typical run, 5.24 g of glycerol (57.0 mmol) were reacted with urea (2.0 g, 33 mmol) [molar ratio glycerol/urea=1.72] for 3 hr at 145° C. under 2 kPa pressure in presence of Catalyst 2a (0.02 g). The reaction mixture was then cooled to room temperature and the carbonate was extracted with acetonitrile (3×3 mL). The acetonitrile phase was separated and urea (1.0 g, 16 mmol) was added to the residual glycerol phase and the reaction continued for 3 more hr at 145° C. The carbonate was extracted again following the same procedure as above (3×3 mL) and the $CH_3CN$ phases were collected. Equimolar amounts of urea (2.0 g, 33 mmol) and glycerol (3.1 g, 33 mmol) were added to the residual mother mixture that was further reacted for 1.5 h at 145° C. The carbonate was extracted with $CH_3CN$. The $CH_3CN$ fractions were combined, the solvent was evaporated in vacuum ? at room temperature (27° C.) and the residual glycerol carbonate was distilled in vacuum.

The final average conversion yield after three runs as above results to be:
90-95% for urea
72-75% for glycerol.

The best selectivity towards carbonate of the converted glycerol is:
90-96% formed glycerol carbonate.
The total extracted glycerol carbonate is
90-95% of the converted glycerol.

The best yield as isolated pure glycerol carbonate (solvent extraction followed by distillation) is 65-72% of the starting glycerol.

In a similar way Catalyst 1, 2, 3 and 4 were used to produce glycerol carbonate with the following isolated yields: Catalyst 1, 50±5%; Catalyst 2, 60±5%; Catalyst 3, 51±5%; Catalyst 4, 40±3%.

Example 2

In a typical run 10 g of glycerol (109 mmol) were reacted with urea (6.0 g, 100 mmol) in presence of Catalyst 2a (0.025 g) at 140° C. at atmospheric pressure in a round bottomed flask connected to a vapor condenser (cooled at −10° C.) while $N_2$ was slowly bubbled through the reacting mixture in order to eliminate $NH_3$. The reaction was carried out for 3 h: the condenser greatly reduces the loss of the solvent (glycerol) that leaves the reaction flask transported by the gas stream. The reacting mixture was cooled to 30° C., added with $CH_3CN$ (5 mL) and kept under vigorous stirring for 15 min. The $CH_3CN$ phase was separated (by decantation) and the reaction continued as reported above. Such procedure was repeated two more times by adding at each new run an equimolar amount of urea and glycerol (50 mmol per each reagent). The $CH_3CN$ phases were collected and evaporated in vacuum and the residual glycerol carbonate (45% with respect to the starting glycerol) was distilled in vacuum to afford 40% pure glycerol carbonate. This methodology allows to work at ambient pressure and uses the $N_2$ flow for the elimination of $NH_3$ but the overall yield is slightly lower than when working in vacuum.

Similarly Catalyst 1, gave 30±3%; Catalyst 2, 40±5%; Catalyst 3, 32±5%; Catalyst 4, 30±5 conversion of glycerol into the relevant isolated carbonate.

Example 3

In a typical run 10 g of glycerol (109 mmol) were reacted with urea (6.0 g, 100 mmol) in the presence of Catalyst2a (0.8% w/w with respect to glycerol) in presence of acetophenone (5 mL) at 145° C. in a round bottomed flask at ambient pressure connected to a vapor condenser (water cooled at 20° C.) while $N_2$ was slowly (50-60 bubbles/min) bubbled through the reacting mixture in order to eliminate $NH_3$ that was then trapped in water. The condenser greatly reduces the loss of the solvent that leaves the reaction flask transported by the gas stream. The reaction was carried out for 3 h, the reacting mixture was cooled to 30° C., and the extraction solvent phase was analysed by GC-MS and the reaction continued for 2 more h. The solvent was analysed as above and the reaction continued as reported above, until the formation of glycerol carbonate was maximized. The solvent phase was finally collected and a fresh amount of the solvent (5 mL) added and the sequence repeated. The solvent phases were mixed together and evaporated in vacuum and the residual glycerol carbonate (45-55% with respect to the starting glycerol) was distilled in vacuum to afford 40-50% pure glycerol carbonate.

This methodology allows to work at ambient pressure and combines the $N_2$ flow for the elimination of $NH_3$ and the use of selective solvent for the continuous extraction of the carbonate. The solvent must be a high boiling solvent in order to avoid substantial losses of said solvent due to the use of a nitrogen stream.

The reaction above with Catalyst 1 gave 30±2%; with Catalyst 2, 40±5%; Catalyst 3, 30±4%; Catalyst 4, 32±5% of isolated glycerol carbonate.

Example 4

In a typical run 10 g of glycerol (109 mmol) were reacted with urea (6.0 g, 100 mmol) in the presence of Catalyst2a (0.8% w/w with respect to glycerol) and of a high boiling extraction solvent such as iso-valeronitrile (5 mL) at 130° C. in a round bottomed flask at ambient pressure connected to a water-cooled vapor condenser while $N_2$ was slowly (30 bubbles/min) bubbled through the reacting mixture in order to strip $NH_3$ which is then trapped in water. The condenser greatly reduces the loss of the solvent that leaves the reaction flask transported by the gas stream. The reaction was carried out for 1 hr, the reacting mixture was cooled to 30° C., and the extraction solvent phase was analyzed by GC-MS. The formation of 4.5 wt % of glycerol carbonate (with respect to the starting glycerol) was determined. The reaction was continued for 2 more h in the same reactor. The solvent was analyzed as above and the formation of a total amount of 10.5% of glycerolcarbonate was determined. and the reaction continued as reported above, until the formation of glycerol carbonate was maximized. The solvent phase was finally collected and a fresh amount of the solvent (5 mL) added and the sequence repeated. The solvent phases were mixed together and evaporated in vacuum and the residual glycerol carbonate (25-30% with respect to the starting glycerol) was distilled in vacuum to lead to 20-25% pure glycerol carbonate.

Measurements confirmed that 55% of the ammonia produced was trapped in water. Some ammonia was probably lost due to the poor design of the trap at lab scale.

Examples 3 and 4 show that the conversion yield depends on the reaction temperature, that decides the selection of the extraction solvent: higher the boiling point of the solvent, higher the conversion yield of glycerol. For example isovalerinitrile (bp 130° C.) allows to work only at 130° C. and the best yield is 25-30% while acetophenone (bp 202° C.) allows to work at 145° C. and the yield is increased to 40-50% of glycerol carbonate.

Example 5

In a typical run 10 g of glycerol (109 mmol) were reacted with urea (6.0 g, 100 mmol) in the presence of $MgSO_4$ (0.8% wt/wt with respect to glycerol) in presence of a high boiling extraction solvent such as iso-valeronitrile (5 mL) at 130° C. in a round bottomed flask connected to a vapor condenser (water cooled at 20° C.) while $N_2$ was slowly bubbled through the reacting mixture in order to eliminate $NH_3$. The conditions were the same as those described in Example 4. At the end of the reaction the catalyst formed a sludge with the solvent and products that made almost impossible the recovery of the catalyst. The extraction of glycerol carbonate was carried out with the addition of further isovaleronitrile (5 mL) and shown to be equal to 8.8%.

Example 6

The reaction of examples 4 and 5 was carried out with ZnO as catalyst that dissolved completely in the reaction mixture. The same amounts of glycerol, urea and catalyst as in examples 4 and 5 were used. Also in this case the catalyst could not be recovered from the reaction mixture as it was completely dissolved in the solvent. The yield of recovered glycerol carbonate was 7.7%.

In the same conditions catalyst 2a gives a yield of 10.8%.

Examples 4, 5, and 6 show that the process of the invention with an extracting solvent described here can be used with several catalyst. The recovery of the catalyst depends on its nature.

The invention claimed is:

1. Process for synthesizing polyol carbonate which comprises: (a) reacting polyol with urea in the presence of a catalyst selected from the group consisting of ZnO, $MnSO_4$, $ZnSO_4$, $MgSO_4$, $FeSO_4$, α and γ-Zr-phosphate, and γ-Ti-phosphate, wherein the reaction of step (a) is heterogeneous and the catalyst is a solid at the operating conditions, and (b) extracting $NH_3$ and extracting polyol carbonate from the reaction medium in step (a) and/or step (b) with a selective solvent for polyol carbonate.

2. Process according to claim 1, in which:
the temperature comprises between 90° C. and 200° C. and the pressure comprises between 2 and 200 kPa.

3. Process according to claim 1 in which the selective solvent has a solubility for polyol carbonate as compared with its solubilities for polyol and urea such that the ratios polyol solubility/polyol carbonate solubility and urea solubility/polyol carbonate solubility are respectively less than 8% and less than 15%.

4. Process according to claim 3, in which the selective solvent is selected from the group consisting of compounds comprising nitrile functionality and compounds comprising ketone functionality.

5. Process according to claim 4 in which the selective solvent is selected from the group consisting of acetonitrile, propionitrile and iso-valeronitrile.

6. Process according to claim 1, in which the catalyst is α and γ-Zr-phosphate or γ-Ti-phosphate.

7. Process according to claim 1 conducted in a compact mode in which the polyol-urea reaction is carried out in the presence of the selective solvent.

8. Process according to claim 7 conducted in a continuous compact mode in which reaction of the polyol-urea and extraction of the polyol carbonate are simultaneous.

9. Process according to claim 7 conducted in a discontinuous compact mode in which the extraction of the polyol carbonate is carried out at the conclusion of each run.

10. Process according to claim 7 carried out at a pressure between 30 and 200 kPa.

11. Process according to claim 1 conducted in a sequenced mode in which the polyol-urea reaction is carried out without the selective solvent and the reaction medium is transferred into an independent zone where the selective solvent is added.

12. Process according to claim 11 conducted in a discontinuous sequenced mode in which the whole reaction medium is transferred into the independent zone where the selective solvent is added.

13. Process according to claim 11 conducted in a continuous sequenced mode in which only a part of reaction medium is transferred into the independent zone where the selective solvent is added, fresh reagents being introduced into the reactor in order to maintain its level of reagents.

14. Process according to claim 11 carried out at a pressure comprised between 2 and 100 kPa.

15. Process for synthesizing polyol carbonate which comprises reacting polyol with urea in the presence of a catalyst comprising γ-Zr-phosphate or γ-Ti-phosphate and extracting produced $NH_3$.

16. Process according to claim 2 wherein, said temperature is between 130-145° C. and said pressure is between 10 and 120 kPa.

17. Process according to claim 3 wherein, said rations are less than 2% and 10% respectively.

18. Process according to claim 7, wherein said pressure is between 60 and 150 kPa.

19. Process according to claim 11 wherein said pressure is between 4 and 20 kPa.

* * * * *